United States Patent [19]

McDowell

[11] Patent Number: Plant 5,911

[45] Date of Patent: Mar. 24, 1987

[54] PECAN TREE NAMED MCLEON

[76] Inventor: Gilbert McDowell, Rte. 2, Nevada, Mo. 64772

[21] Appl. No.: 772,270

[22] Filed: Sep. 3, 1985

[51] Int. Cl.[4] ..... A01H 5/03

[52] U.S. Cl. ..... Plt./31

[58] Field of Search ..... Plt./31

*Primary Examiner*—Robert E. Bagwill

*Attorney, Agent, or Firm*—Wm. A. Snow

[57] ABSTRACT

A new and distinct variety of pecan tree distinguished by its resistance to cold weather and its ability to produce a high yield nut crop farther north, i.e. as far north as Nevada, Mo., and more consistently than any southern variety, the fruit ripening in midseason all at the same time and being exceptionally easy to harvest. This new pecan tree is resistant to pecan weevils and scab disease prevalent in other varieties in the same orchard, and because of its open center growth with widely branching limbs, there is good air circulation between the leaves which materially reduces the incidents of mildew or fungus diseases. The growth rate of this tree is unusually rapid with nut production occurring four years after being grafted. The nuts generally run about fifty-five to the pound and the cracking percentage in approximately fifty-five to sixty percent.

3 Drawing Figures

BACKGROUND OF THE NEW TREE

It has long been an object of northern (as distinct from southern United States) nut growers to develop, by breeding and selection among cultivars, a pecan tree that would extend the range of good commercial pecan production further northward. In 1960, in an orchard near Neosho, Mo., I gathered nuts from a rather hardy tree of the variety of southern pecan tree known as "Moore", this variety of pecan being a well known variety that had been used for years as root stock for grafting commercial trees in nurseries in the South. In this orchard, there were several varieties of grafted pecan trees surrounding the "Moore". To get a grove of "Moore", I would graft from "Moore" trees. I planted three hundred selected nuts from this tree, these nuts having been randomly pollinated by other trees in this orchard. This planting was made in the spring of 1961. All pecans are Carya Illinoensis G.m.D.

In 1963, after a two year growing period, selected ones of these seedlings were transplanted by me into a plot at fifty foot spacing intervals, and in 1972, the eleventh growing season, these trees started bearing nuts. Late in the 1972 season, as I was driving along the row of seedling trees, I noticed that Tree No. 19 was far superior to the remaining stand of these trees, particularly in that the nuts appeared to be much larger and that the husks were actually curled up into a bell shape displaying the nuts which were much longer and larger than any other variety in the orchard where this Seedling No. 19 had been grown and matured.

In 1974, because of the superior characteristics of the No. 19 seedling, several grafting scions of that tree were grafted onto native pecan root stock. Most of these trees, that were grafted scions of No. 19, came into production during the years 1977 and 1978.

This new tree herein disclosed has been asexually reproduced by me since 1974 by grafting and budding, the present method of propagation being by both graft and budding and is done at Nevada, Mo., and it has been observed that the distinguishing characteristics of this new pecan variety hold true from generation to generation and appear to be firmly fixed.

DESCRIPTION OF THE DRAWINGS

My new variety of pecan tree is illustrated by the accompanying full color photographic drawings, in which:

The upper photograph on the first sheet is a full view of my new variety illustrating the tree in the summer.

The lower photograph shows the same tree in the late fall after the leaves have left the tree.

The second sheet discloses a comparison of pecans between one nut of the Starks "Hardy" and one nut from the tree of the present application, the larger one.

The colors shown are as nearly true as is possible to obtain by conventional photographic procedures.

DESCRIPTION OF THE NEW TREE

Growth Habit

Vigorous and spreading with an open crown and numerous bearing branches having an angle of attachment to the tree trunk of about 70° from the vertical and spaced along the trunk of the tree about 20 to 30 inches apart. This tree has a growth rate of about 15 to 30 inches per year in height for the first few years reaching an average height of about 20 feet at the age of eight years and begins production in about three to four years from the time of grafting onto root stock.

Foliage

The leaves of this new tree are unusually large and more abundant than those of most pecan trees. The form of the leaves is odd pinnate, those of the tree at the age of about eleven years being about 18.8 cm. long and commonly having 14.2 unusually large leaflets each averaging about 1.8 cm. in width and 5.5 cm. in length. The leaflet shape is oblanceolate with an acuminate apex and serrated margins. The leaves of this new tree are also noted to be lighter in color and larger than other pecan trees native to the area, or growing in the same orchard. The under side of the leaves appears to be less slick than other pecan tree leaves and also appears to be thicker in cross-section than conventional leaves and pubescence on the under side of the leaves is considered to be an important characteristic for identifying this new tree.

Stark's "Hardy", wherein the leaf length was 15.6 cm. and having only 11 leaves each of a length of 4.7 cm. and a width of 1.1 cm., was compared to the leaves of the instant tree.

Buds

The buds of this new tree are generally three and sometimes four in number and appear above each leaf crotch. The bud break occurs about one week later than most northern varieties, thereby having the advantage of a lesser possibility of frost damage.

Nuts

Ripening Habit: Ripening maturity occurs about November 1, running about ten days later than the nuts of native trees. The nuts generally grow in clusters of three to five, all clusters ripening together and all nuts are therefore harvested at the same time.

Size: The nuts of this new tree are medium large, averaging about 3.8 cm. long and about 2.1 cm. in diameter. The average weight is 6.5 grams with a standard deviation of about 0.52 grams. The nuts generally run about fifty-five to the pound and the cracking percentage is approximately fifty-five to sixty percent.

Shell and Husk: The shell and husk of the nuts of this new tree are thinner than most of the well known varieties. Shell thickness is similar to that of the "Barton" pecan, easy to crack and very brittle, and once cracked can be readily peeled by the use of the thumb nail.

Shelling Quality: Cracking tests have demonstrated an average of about fifty-six pounds of kernels resulting from one hundred pounds of whole nuts. Some year-to-year variation has been observed and the highest percentage crackability observed has been about 59%.

Disease and Insect Resistance

My new variety of pecan tree has a very open crown and smooth bark and because of these features, the resistance to disease and insects is considerably enhanced. The resistance to pecan weevils appears to be absolute and by observation each year since 1972, they have never been found in the nuts of this new variety while they were present in other varieties growing in the same orchard. Likewise, resistance to scab disease appears to be complete in the new pecan tree whereas scab disease has been found to infect other varieties in the same orchard.

Particular advantages of my new pecan tree reside in the ability to grow and retain all of its novel characteristics, including consistently abundant production of high quality nuts, in growing areas much farther north than has been heretofore practical for a nut of this size and high quality. Also, it has been observed that my new pecan tree has matured by the average picking date every year since it has come into production, the normal picking date considered to be the first week in November. Furthermore, my new pecan trees have been found to be exceptionally easy to harvest even as compared with the native pecan, in that the shuck tends to split open to release the nut much easier than the native variety. Also, in a year when frost is considered to be early, the nuts of other varieties will frequently tend to turn black and the husks will stick tight or will not peel off to release the nut. This has never happened with my new pecan tree herein disclosed.

I claim:

1. A new and distinct variety of pecan tree, substantially as herein shown and described, characterized by its prolific production of large size and very thin shelled nuts, its consistent ripening period with all nuts ripening together for harvesting the full crop at the same time, its relatively high shelling quality, and its resistance to cold and frost and abundant production of high quality nuts in orchard locations considerably farther north, i.e. as Vernon County, Mo., than heretofore believed to be practical, and its resistance to disease.

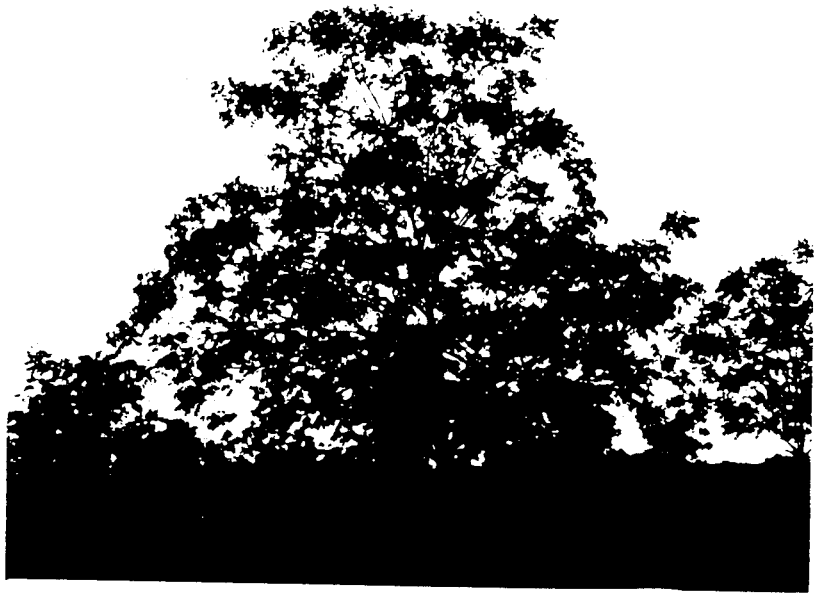
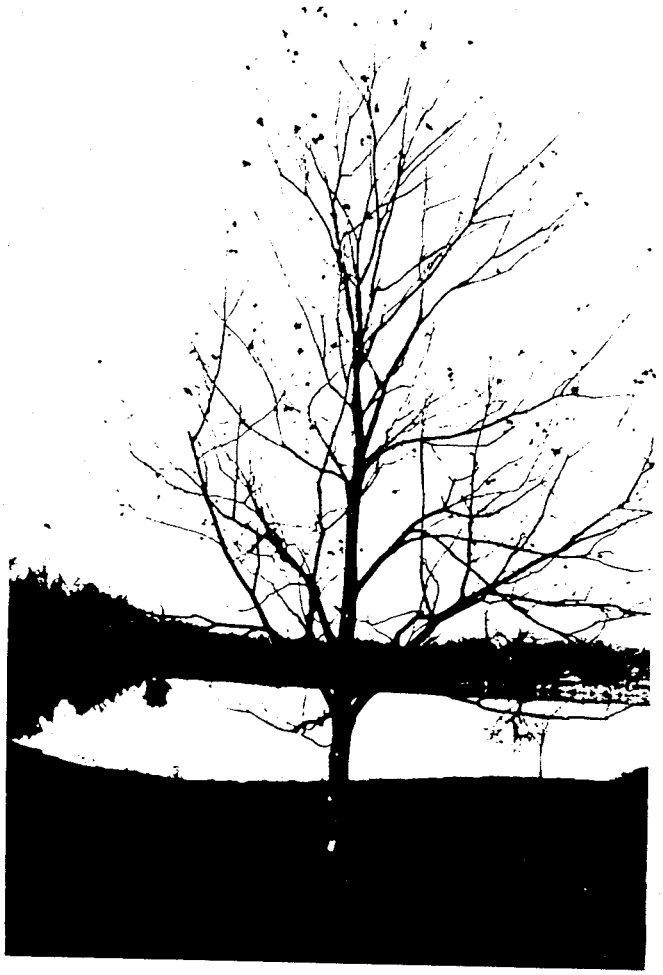

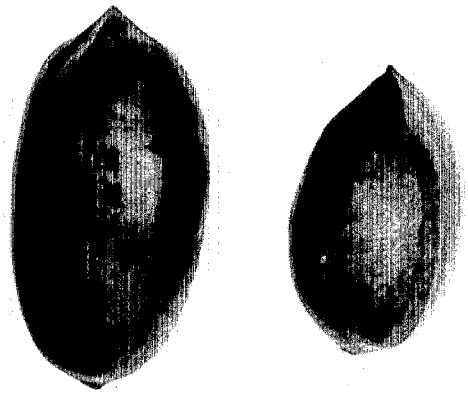

* * * * *